United States Patent [19]

Sjöholm et al.

[11] 4,061,466
[45] Dec. 6, 1977

[54] BIOLOGICALLY ACTIVE COMPOSITION AND THE USE THEREOF

[76] Inventors: Ingvar Gösta Holger Sjöholm, Tallmovagen 14, S-752 45, Uppsala; Nils Roger Lindmark, Glimmervagen 9 B, S-752 41 Uppsala; Bo Magnus Ekman, Granitvagen 6 B, S-752 43 Uppsala, all of Sweden

[21] Appl. No.: 621,888

[22] Filed: Oct. 14, 1975

[30] Foreign Application Priority Data

Oct. 16, 1974 Sweden ............................ 7412990
Oct. 16, 1974 Sweden ............................ 7412992
Oct. 16, 1974 Sweden ............................ 7412993

[51] Int. Cl.$^2$ .................... G01N 33/16; G01N 31/14
[52] U.S. Cl. ................................ 23/230 B; 23/230.6; 195/63; 195/103.5 A; 195/DIG. 11; 252/408; 260/112 R; 424/1; 424/1.5; 424/12
[58] Field of Search ............... 23/230 B, 230.3, 230.6; 195/63, 68, DIG. 11; 424/1, 1.5, 12; 260/112 R; 252/184, 316

[56] References Cited

U.S. PATENT DOCUMENTS 3,793,445  2/1974  Updike et al. ........................ 424/12
3,850,752  11/1974 Schuurs et al. ............... 195/103.5 R
3,859,169  1/1975  O'Driscoll et al. .................... 195/63

OTHER PUBLICATIONS

Nilsson et al., *Biochimica Biophysica Acta*, vol. 268, pp. 253–256, (1972).
Chem. Abstr., v.81:87177g, (1974).
Chem. Abstr., v.81:165575b, 165576 c, (1974).

*Primary Examiner*—Sidney Marantz
*Attorney, Agent, or Firm*—Fred Philpitt

[57] ABSTRACT

Immobilized biologically active substances comprising microporous, spherical particles in gel form and in the form of a three-dimensional network. These particles contain the biologically active substance entrapped in the meshes of the network. The particles have sizes below 10 $\mu$m and the average diameter of the particles is in the range of from 0.5 to 4 $\mu$m, preferably 1 $\mu$m. The biologically active substance is capable of exerting its biological activity against substances which cannot penetrate into the meshes of the network of the particles. Preferably, the particles are gel grains obtained by copolymerization of acrylic compounds with cross-linkers. The immobilized biologically active substances are used for labelling or separation of cells, cell fragments, viruses or tissue structures having specific receptors or of substances having specific surface structures.

11 Claims, No Drawings

BIOLOGICALLY ACTIVE COMPOSITION AND THE USE THEREOF

The present invention is concerned with an immobilized active substance and the use thereof. More particularly, the invention relates to an immobilized biologically active substance consisting of microporous, spherical particles in gel form and in the form of a three-dimensional network, said particles containing the biologically active substance entrapped in the meshes of the network, and the use of the substance as a reagent for the quantitative determination of a component in a biospecific system and for the labelling or separation of cells, cell fragments, viruses or tissue structures with specific receptors and substances having specific surface structures.

Biochim. Biophys, Acta 166 (1968), pages 29 - 39 discloses the preparation of immobilized polynucleotides by dispersion polymerisation of an aqueous solution of acrylamide and N,N'-methylenebisacrylamide, said solution also containing a polyneucleotide. The polymerisation results in the formation of microporous, spherical particles in gel form having a diameter of 50 - 250 μm and having the structural form of a three-dimensional network which has the polynucleotide entrapped in its meshes. A fraction in the range of from 150 - 200 μm is used for column chromatography, elution taking place with solutions containing an enzyme having such a molecular size as to be capable of penetrating into the pores of the particles.

According to the present invention it has now been found that it is possible to immobilize biologically active substances by means of microporous, spherical particles in gel form in such a manner as to make these substances capable of exerting their biologically activity also against substances which cannot penetrate into the network of the particles to a very high degree, thereby to secure a very wide use of the immobilized, biologically active substances. These advantages are reached according to the invention by imparting a size to the particles below 10 μm and an average diameter of 0.5 - 4 μm, preferably 1 μm.

In contrast to what applies to the previously known immobilized substances, the particles according to the invention are sufficiently small to insure that a great part of the molecules of the biologically active substance is not entirely within the network of the particles but project partially from the latter. It is considered particularly surprising that it was possible to achieve an effective immobilization of the biologically active substance without the latter being within the particles.

On the basis of what has been set forth above, the invention is concerned with an immobilized, biologically active substance consisting of microporous, spherical particles in gel form and in the form of a three-dimensional polymeric network, said particles containing the biologically active substance entrapped in the meshes of the network. What characterizes the invention is that the particles have a size below 10 μm and an average diameter of 0.5 - 4 μm, preferably 1 μm, thereby to render the biologically active substance capable of exerting its biological activity against substances which are not capable of penetrating into the network of the particles.

Primarily, the particles consist of a copolymer of a low molecular acrylic compound or of 1-vinyl-2-pyrrolidinone with a low molecular divinyl compound, which latter functions as a cross-linking agent. By the expression "low molecular" is meant that the compound suitably contains no more than 10 carbon atoms. Preferably, the acrylic compound contains no more than 4 carbon atoms while the divinyl compound is preferably N,N'-methylenebisacrylamide.

Suitable low molecular divinyl compounds may be any of those known low molecular compounds which present two terminal ethylenically unsaturated groups. Examples of such low molecular divinyl compounds are N,N'-methylenebisacrylamide, diethyleneglycoldivinyl ether, ethyleneglycoldimethacrylate and divinylsulphone.

Preferred particles comprise a copolymer of an acrylic compound having the formula

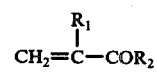

wherein $R_1$ stands for hydrogen or methyl and $R_2$ is hydroxyl or $-NHR_3$, wherein $R_3$ is hydrogen or a straight or branched alkyl group containing 1 - 6 carbon atoms, said group being unsubstituted or substituted by a hydroxyl or oxo group, with N,N'-methylenebisacrylamide. Especially preferred are copolymers or acrylic acid and/or acrylamide with N,N'-methylenebisacrylamide.

Examples of low molecular acrylic compounds useful according to the invention are acrylamide, methacrylamide, N-hydroxymethylacrylamide, 2-hydroxyethylmethacrylate, acrylnitril, acrylic acid, N,N-dimethylaminoethylmethacrylate and glycidylmethacrylate.

The biologically active substance is composed of macromolecules such as proteins, polysaccharides, polyamino acids, nucleic acids separately or in mixtures with each other. The biologically active substance may be either unmodified or conjugated with radioactively labelled substances, colourants or low molecular weight molecules. The active substance may also be labelled itself with a radiation-producing atom or atom group, a enzyme or a colour-producing group. An indirect labelling may also be achieved by incorporating the labelling substance into the particles together with the biologically active substance.

Low molecular weight molecules can be immobilized by being bound to macromolecules immobilized in the particles by chemical reaction or adsorption.

In principle, the particles are prepared according to methods known within the art of dispersion polymerisation. In detail, the preparation can take place in the following manner:

An aqueous solution of the monomers to be polymerised is mixed with a solution of the biologically active substance (a macromolecule or a low molecular weight compound coupled to a macromolecule) to be immobilized. An organic phase, for example consisting of a mixture of toluene and chloroform in the ratio 3:1, is placed in a reaction vessel together with a suitable emulsifier. The air over the organic phase is expelled by nitrogen gas. A catalyst is added to the monomer solution which is cooled to reduce the reaction speed and this solution is rapidly cast into the organic phase which is treated intensively by an effective homogenisator. Particles having sizes below 1 μm can be manufactured in this manner. In the polymerisation process, the temperature should not be permitted to exceed +40° C, which means that biological molecules remain biologically active.

The porosity of the particles can be varied by changing the concentration in the solution of starting monomers and by changing the concentration of cross-linking divinyl compound in the monomer mixture. The surface charge can be varied from uncharged to positive or negative charge by suitable selection of concentration and type of monomers. By introducing charged groups in the gel polymer in the polymerisation the obtained charged particles can be caused to repel each other to prevent aggregation of the latter which is important in view of the use of the immobilized, biologically active substance. The monomer solution can be added with fluoroscent derivatives of monovinyl monomer, said monomer being incorporated in the gel skeleton in the polymerisation and making the particles fluorescent. Organic molecules can be coupled by chemical reactions to the immobilized, biologically active substance within the particles also after the polymerisation.

The immobilized, biologically active substance can be lyophilized or dried with ethanol and then stored for years at room temperature.

A different aspect of the invention is concerned with the use of an immobilized, biologically active substance according to the invention as a reagent for the quantitative determination of a component in a biospecific system, said system containing the biologically active substance as a component, by means of agglutination, immunometric, immunoassay- or cell receptor assay-methods.

The invention is also concerned with agglutination, immunometric, immunoassay- and cellreceptor assay-methods for the quantitative determination of a component in a biospecific system while using a reagent consisting of a biologically active substance belonging to the biospecific system bound to microporous, spherical particles having the structural form of a three-dimensional network. The invention is characterized by using particles having sizes below 10 $\mu$m and an average diameter of 0.5 – 4 $\mu$m, preferably 1 $\mu$m, said particles containing the biologically active substance in immobilized condition and entrapped in the meshes of the three-dimensional network. In the above use and method the immobilized, biologically active substance may be labelled by an atom or an atom group capable of emitting radiation, an enzyme or a colour-producing group.

The principle of agglutination reactions is that the substance to be determined is detected by its specific interaction with molecules situated on reagent particles, said interaction resulting in that adjacent particles are bonded together to a network which can be observed by visual means. In the agglutination technique there is made a serial dilution of the sample and a known concentration of the substance to be determined in special disposable plastic containers. By providing the particles with charges by copolymerisation of charged vinyl compounds, particles are obtained which do not form aggregates spontaneously. A standardized quantity of reagent particles according to the invention is added to all dilutions and to containers having only buffer as a blank. When the sample contains the determinable component direct agglutination results in the particles being bonded together over the molecules of the component thereby to form a uniform carpet over the bottom surface of the plastic container. If on the other hand the sample is negative, the particles will settle to the bottom of the container to thereby form a small, sharply restricted zone.

In direct so-called inhibition techniques are based on a competition between the same molecules immobilized in the particle and the molecules of the sample to a limited amount of added macromolecules biospecific to the actual molecules. Quantification takes place in these methods semiquantitatively by comparing the dilution degree at agglutination of the blank with that of the sample. If the particles are made uncharged the agglutination reaction will be observable on a plane surface.

Immunometric, immunoassay- and cellreceptor assay-methods are based on a specific interaction between the biospecific molecules and their ligand. By providing the biospecific molecule and the determinable substance with suitable labels the degree of specific interaction can be quantified, frequently after a separation stage. The method can be used for the determination of one of the components of an interacting system.

In competetive protein binding techniques the immobilized, biologically active substance according to the invention is used in the following manner: There is first added preferably a label to a diluted or undiluted sample, said label being radioactive or enzyme-labelled form of the substance to be quantified. Microparticles with immobilized biospecific proteins are then added in a slightly lower amount than the label and incubation is permitted to take place until equlibrium has been reached. The microparticles can be separated readily from the solution by strong centrifugation. The particles are washed with buffer and centrifugated some times more. An enzymatic or radioactive measurement of the sample yields an answer to the question of how great a part of the label which has been bound to the component has been immobilized in the particles. Another possibility is to quantify the label in the supernatant after the first centrifugation process. The amount of the substance can be quantified from a standard curve obtained by first adding known amounts of the substance to be determined to a constant amount of gel particles and label.

In imminometric techniques the antibodies or receptor molecules are labelled and added in an excess, after which the incubation is permitted to take place until equilibrium has been reached. Microparticles with a determinable substance immobilized according to the invention are then added in order that labelled antibodies or cell receptors which have not reacted may be separated off. After centrifugation in a usual table centrifuge, a fixed part of the overlying phase can be investigated and the substance quantified after establishing a standard curve by means of known amounts of the substance. Quantification can also take place on the washed particles.

With respect to competitive binding techniques for quantitative determination the use of an immobilized, biologically active substance according to the invention results in the following advantages as compared with previously used reagents:

Chemically inert particles having a high mechanical stability and a well defined size below 10 $\mu$m can be prepared cheaply and simply with the biospecific molecule or ligand immobilized even in the polymerisation process.

After lyophilization or drying with ethanol the particles can be stored with the immobilized molecule biologically intact for several years at room temperature.

By variation of the surface charge it is possible to simplify the agglutination reaction by permitting the latter to take place in wells sloping towards the centre in plastic plates of the disposable type.

Biospecific proteins or ligands can be immobilized in the polymerisation process without the great losses which are obtained in the mechanical desintegration of polymer blocks.

By immobilizing suitable polymers in the polymerisation these methods are applicable to low molecular weight substances by coupling the latter to the macromolecules by a simple previously known conjugation method.

The ability of the polyacrylamide to adhere to glassy surfaces can be utilized for eliminating the centrifugation moment.

The particles are entirely spherical and of uniform size which means that they will be practical to use and easy to dose in contrast to particles obtained after disintegration of great polymer blocks. Covalent coupling of the biospecific molecules has not been used for the immobilization because such coupling would result in losses of biological activity.

A further aspect of the invention is concerned with the use of an immobilized, biologically active substance according to the invention for labelling cells, cell fragments, viruses and tissue structures with specific receptors or substances having specific surface structures, one of the receptors being specifically directed to the biologically active substance or one of the surface structures reacting specifically with said biologically active substance and said substance being labelled with an atom or atom group capable of emitting radiation, an enzyme or a colour-producing group.

In accordance herewith, the invention is also concerned with a method of labelling cells, cell fragments, viruses, or tissue structures with specific receptors or substances having specific surface structures by biospecific interaction with a reagent consisting of a biologically active substance bonded to a solid carrier, one of the receptors being specifically directed against said substance or one of the surface structures reacting specifically with said biologically active substance, said biologically active substance being labelled with an atom or atom group capable of emitting radiation, an enzyme or a colourproducing group. The method is characterized by using as a solid carrier microporous, spherical particles in the structural form of a three-dimensional network, said particles presenting sizes below 10 $\mu$m and an average diameter of 0.5 – 4 $\mu$m, preferably 1 $\mu$m, said particles having the biologically active substance entrapped in immobilized condition in the meshes of the three-dimensional network.

The labelling can be used for different type of studies, for example a study of surface structures with cells. A number of different labels for the immobilized, biologically active substance can be used depending on the type of studies to be carried out and available equipment. By labelling particles with radioactive isotopes detection and quantification can take place in liquid or gamma scintillation counters. Labelling of the particles can also be carried out with fluorescent substances of the type fluorescein or rhodamine and can be observed in a fluorescence microscope. For electron microscopic studies proteins having a high electron density of the type ferritin can be immobilized in the particles in the preparation thereof and can thereby detected in an electron microscope. Particles having very small particle sizes would then be used. With respect to tissue studies, enzymes such as horseradish peroxidase can be immobilized in the particles and detected over specific enzymatic colouring reactions observable in a microscope. The polymer grains with the immobilized liqand and label are added and incubated in a cell suspension. The excess of the particles is removed and a suitable substrate such as benzidine is added, the oxidation of the latter being then detected. This method makes it possible to determine the amount of cells in a population with a certain surface structure.

According to a further aspect of the invention, the latter is concerned with the use of an immobilized, biologically active substance according to the invention for the separation of cells, cell fragments, viruses or tissue structures with specific receptors or substances with specific surface structures from a substance mixture containing such cells, cell fragments, viruses, tissue structures or substances by permitting the biologically active substance to interact specifically with the cells etc. to formation of a conjugate which is then separated from remaining components of the substance mixture by methods based on differences in density and the adsorption of the particles to glass walls.

The invention is also concerned with a method of separating cells, cell fragments, viruses or tissue structures with specific receptors or substances with specific surface structures from a substance mixture containing such cells, cell fragments, viruses, tissue structures or substances by specific interaction with a reagent consisting of a biologically active substance bonded to a solid carrier, to which one of the receptors is specifically directed or with which one of the surface structures reacts specifically to formation of a conjugate which is separated from remaining components in the substance mixture by methods based on differences in density and the adsorption of a carrier to glass walls. The invention is characterized by using as a solid carried microporous, spherical particles in gel form and having the structural form of a three-dimensional network, said particles having sizes below 10 $\mu$m and an average diameter of 0.5 – 4 $\mu$m, preferably 1 $\mu$m, and said particles having the biologically active substance entrapped in immobilized condition within the meshes of the three-dimensional network.

In the above use and methods the biologically active substance may be labelled with an atom or atom group capable of emitting radiation, an enzyme or a colour-producing group.

For the separation of biological cells having a certain surface structure in a cell population, micro particles with a suitable density and having the molecule (ligand) interacting specifically with that type of cells immobilized in the micro particles can be used. To a cell suspension there are added micro particles having their ligand immobilized in the particles and incubation is permitted to take place until equilbrium has been reached in the system. The sample is stored in a suitable density gradient in a centrifuge tube of plastic on the top of the gradient. Due to the interaction of cells having a specific surface structure with the ligand micro particles these cell complexes will obtain a density different from that of the free cells. Separation takes place when the sample tubes are centrifugated in a cooled centrifuge at a suitable number of revolution until the separation is obtained. Two different layers are obtained in the tube, the heavier fraction being nearest to the bottom.

The density of the micro particles can be varied by changing the concentration of the low molecular weight acryl monomer between 5 and 50%. It will thereby be possible to separate different kinds of cells having different surface structures by selecting micro particles with suitable density and by selecting density gradient. The separation between the different cell types can be observed visually by labelling the different particles with colouring substances. Such conditions as centrifugation time and density gradient can be determined in this manner. By immobilizing the ligand to the particles over immobilized dextran or collagen the cells can be separated from the particles in a saving manner by enzymatic treatment with, respectively, dextranase or collagenase.

A further possibility of using ligand particles for the separation of cells is to use the ability of the polyacrylamide of being adsorbed to glassy surfaces. Ligand polyacrylamide particles are distributed uniformly over the glass surface in a cultivation vessel. The cell suspension is then added to the vessel thereby to cause cells having a specific surface structure to attach to the ligand particles. By rinsing away the excess of remaining cells after the necessary incubation process it will be possible to obtain a very homogeneous cell suspension. After the addition of nutrient medium that suspension can be cultivated and the process can be repeated if the cells thus obtained are heterogeneous.

Biologically active substances immobilized according to the invention can be used for biospecific isolation of certain compounds of mixture according to the same methods which are already in use with respect to biospecific adsorbents covalently bound to different matrises. Chromatographic and batch-wise processes can be used.

The advantages are obvious to any person skilled in the art when new research prospects appear in the field of cell biological research.

The micro particles, to which the biologically active substance has been immobilized, do not present any unspecific or poisonous effect on biological cells.

By varying the density and colour of the particles at least two different types of cells can be separated by centrifugation and when the particles are coloured the suitable conditions for the separation can readily be determined by trials.

The ligand can be immobilized to the particles and released from the latter proteolytically or by another enzymatic digestion of the immobilized polymer to which the ligand is covalently coupled by means of enzymes which do not impair the surface structure of the cells. In many cases, particularly when specific molecules are to be prepared in pure form from a mixture thereof, the interaction with the particles can be interrupted readily by varying the properties of the medium such as temperature, pH, salt concentration etc. In these cases the micro particles can be reused after washing.

Ligand particles adsorbed to the glass surface of the cultivation vessel can be separated and cultivated in the same vessel without moving the cells and subjecting them to risk of contamination.

In connection with studying the surface structure of a cell, micro particles with immobilized ligand can be used for studying different cell receptors. Many different organic molecules can be immobilized in the particles.

Two different types of cell structures present within the same cell or cell population can be studied by simultaneous detection of two different labels, such as fluorescein and rhodamine.

The method of preparing the particles insures that the properties of the macromolecules entrapped within the particles are not changed by chemical modification in connection with the immobilization process.

The invention will now be described and illustrated furthermore by a number of examples which are not, however, intended to restrict the invention.

EXAMPLE 1

200 ml of a mixture of toluene and chloroform (150:50 are mixed in a beaker with 0.3 g of an emulsifier consisting of a poly(oxyethylene)-poly(oxypropylene)-poly(oxyethylene)-polymer (Pluronics ® F 68). 30 ml of a solution well blown-through by nitrogen gas and cooled ($+4°$ C), said solution containing acrylamide (6%) and N,N'-methylene-bis(acrylamide) (2%), and 300 $\mu$l N,N,N',N'-tetramethylenediamine are mixed carefully. There are then added 150 mg of albumin and the solution is rapidly mixed with 1 ml of a 10 per cent solution of ammonium peroxodisulphate in water and is cast into the beaker. The mixture is immediately homogenized by an effective emulsifying device made by Silversons (Waterside, Chesham, Bucks., U.K.). The mixture is illuminated by a strong lamp, thereby to cause the polymerisation to polyacrylamide to take place. After centrifugation and washing micro particles having an average diameter of 1 $\mu$m (according to measurements made in a celloscope) with the immobilized albumin are obtained.

EXAMPLE 2

Micro particles with immobilized albumin are prepared in a manner similar to example 1, but with a lower concentration of acrylamide (3%) and bisacrylamide (1%). The size distribution of the obtained particles was the same as in example 1. Experiments showed that the ability of the albumin to bind different drugs such as salicyclic acid and warfarin has not been changed.

EXAMPLE 3

Micro particles with immobilized albumin are prepared in a manner similar to example 1, but with a considerably higher concentration of albumin in the monomer solution (200 mg/ml). The polymerisation process took place as in example 1. The content of albumin of the final particles was high and corresponded to about 25% of the weight of the particles.

EXAMPLE 4

Micro particles were prepared in a manner similar to example 1, but with 7% of acrylamide and 3% of bisacrylamide in the monomer solution and with the albumin changed for Concanavalin A (2 mg/ml). The obtained particles varied in sizes between about 1 and 5 $\mu$m and appeared capable of binding strongly to red blood corpuscles in physiological salt solution. Fluroescein isothiocyanate could also be bonded to the obtained particles very readily.

EXAMPLE 5

Particles prepared according to example 4 with small amounts of human serum albumin modified with fluorescein isothiocyanate together with Concanavalin A.

The obtained particles could be observed readily in a microscope in fluorescent light.

EXAMPLE 6

In a manner similar to example 1 there were prepared particles with protein A from Staphylococcus aureus. The concentration in the aqueous solution was 4 mg/ml. The obtained particles proved capable of getting caught in a Sepharose column to which normal immunoglobulin from human origin (mainly IgG1) had been bound by covalent bonds.

EXAMPLE 7

Dextran having an average molecular weight of about 40,000 had been treated with cyanogen bromide. Glycine was coupled to the dextran by passing through a column consisting of Biogel P-6. The dextran thus modified was immobilized in micro particles in a manner similar to example 1. Different compounds presenting free amino groups could be coupled by covalent bonds (for example insulin) to the carboxylic group deriving from the glycine by means of conventional methods of synthesis. "Insulin micro particles" were then used for studying the insulin receptors of different cells.

EXAMPLE 8

In accordance with the principles given in example 7 also radioactively labelled insulin ($^{125}$I-insulin) was bonded in micro particles. The binding to cells could be quantified more readily by the radioactive radiation.

EXAMPLE 9

Bromosulphophthalein represents a strongly blueviolet dye in alkaline pH which can be coupled by bromosubstitution to different types of polysaccharides, such as crosslinked agarose. In a manner similar to example 1 there were prepared micro particles containing bonded bromosulphophthalein. The particles proved capable of absorbing albumin and ligandine-like proteins from pig liver from solutions thereof. In a similar manner bromosulphophthalein could be coupled to polyethyleneglycol which was then entrapped in micro particles.

EXAMPLE 10

In a manner similar to example 1 poly-1-lysin could be entrapped in micro particles instead of albumin.

EXAMPLE 11

Micro particles were prepared similar to example 1, but with the difference that acrylic acid was substituted for the acrylamide. The micro particles obtained in the same manner as in example 1, varied in sizes up to about 5 $\mu$m. They contained carboxylic groups which render them a negative charge at neutral pH-values, said charge repelling them from other negatively charged bodies. This example proves that the ratio acrylamide:acrylic acid can be varied from 1:0 to 0:1.

EXAMPLE 12

T-lymphocytes were labelled specifically in a mixture of B- and T-lymphocytes by incubating the mixture with micro particles (having an average diameter of 0.5 $\mu$m) for 30 minutes in a buffer at 0° C, said particles containing helix pomatia agglutin - a lectin capable of binding T-lymphocytes specifically - and fluorescence-labelled albumin. The mixture of cells was then washed free from excess of particles by making a suspension in the buffer and centrifuging said suspension. Cells of the mixture of cells which had bonded particles to their surface could be detected in a fluorescence microscope and the content of T-lymphocytes then calculated.

EXAMPLE 13

The experiment was carried out in a manner similar to example 12. Instead of $I^{125}$-modified albumin the particles now contained albumin labelled with fluorescein. The complex of particles and cells was detected by autoradiography.

EXAMPLE 14

The experiment was carried out in a manner similar to example 13. Instead of albumin labelled with fluorescein, the particles now contained ferritin. The complex of particles was detected by using an electron microscope.

EXAMPLE 15

T-lymphocytes were separated from a mixture of cells consisting of B- and T-lymphocytes by incubating the mixture with micro particles containing helix pomatia agglutin for 30 minutes according to example 12. The mixture of cells was then placed as a layer on the top of a sucrose or metrizoate gradient, and after centrifuging for 45 minutes at 30,000 rpm the cells which had not reacted with the particles were found as the lowest zone in the gradient. At the top of the gradient particles which had not reacted with cells were found. In the field between these two zones cells were found which had reacted with particles to a varying degree.

EXAMPLE 16

The experiment was carried out in a manner similar to example 15 except that the particles presented a higher density than the cells due to iodomodified polytryosin having been polymerised into the particles. The order of the zones was the opposite as compared with example 15.

EXAMPLE 17

The experiment was carried out in a manner similar to example 15 except that helix pomatia agglutin had been coupled by covalent bonds to collagent which had been polymerised into the particles. After the T-lymphocytes had been separated by interaction with the particles the cells were again made free from the particles by enzymatic digestion with collagenase.

EXAMPLE 18

Radioimmunassay of morphine

A rabbit-antimorphine-serum commercially accessible was polymerised into particles of polyacrylamide particles (T-C = 7.5 - 5), the average diameter of the particles being 1 - 2 $\mu$m. Before use the micro particles were washed carefully in a 0.05 M phosphate buffer pH 7.5 with 0.15 M NaCl, 0.1% (v/v) Tween 20 and 0.1% (w/v) gelatin. 1 ml of antiserum was sufficient for 20 ml of packed micro particles. The micro particles were diluted twice in a step-wise manner and 0.5 ml of each of the dilutions were placed in an Ellemann tube. 35,000 dpm of tritium labelled morphine were then added to each dilution. The dilution of particles that bonded 50% of the added morphine and was used for the continued operation of analysis. A standard curve was prepared by adding known amounts of nonlabelled morphine to 35,000 dpm of morphine (volume: 0.5 ml). After adding 0.5 ml of particle suspension, the suspension was permitted to stand at room temperature for 4 hours without stirring. The tubes were then subjected to centrifuging in an ordinary table centrifuge at 4,700 rpm for 5 minutes, 0.5 ml of the supernatant was removed by a pipette, and after addition of a scintillation liquid to this quantity the mixture was counted in a scintillation counter. A standard curve was prepared by logit-log plot, making it possible to determine amounts of morphine as low as 5 - 10 μg.

Contents of morphine in samples of serum were determined down to 5 - 10 ng/ml of serum.

EXAMPLE 19

The experiment was carried out in a manner similar to example 18 except that rabbit-antidigoxin-antibodies were polymerised into the particles for the determination of digoxin in serum. The digoxin ws labelled with the isotope I$^{125}$ and amounts down to 0.5 ng of digoxin were determined.

EXAMPLE 20

The experiment was carried out in a manner similar to example 18 except that guinea-pig-antiinsulin-serum was polymerised into the particles for the determination of the polypeptide hormone insulin in serum. The insulin was labelled with I$^{125}$ and amounts of insulin as low as 6.5 uU/ml of serum was measured by the method. However, the analysis consumed slightly greater amount of antiserum than the conventional technique based on the use of solid phase.

EXAMPLE 21

Particles containing a protein from the bacterium S. aureus, said protein being capable of binding immunglobulin G, were addeed to an excess of rabbit-antibovine-serum-albumin (BSA). The excess of antibodies was washed off with 0.05 M phosphate buffer pH 32 7.4 with 0.15 M NaCl and 0.1% (v/v) Tween 20. The particles were diluted in that buffer to 5% (v/v) concentration. 50 μl of BSA solutions strongly diluted to 5 ng/ml were placed on a siliconized glassy surface. 50 μl of the particle suspension were added to each droplet and permitted to react. After about 30 minutes a distinct aggregation of the particles in the solutions of BSA was observed, said aggregation being not possible to observe in the blank sample with only buffer. Amounts of BSA as low as 10 - 15 ng/ml were detected.

EXAMPLE 22

The experiment was carried out in a manner similar to example 21 except that dinitrophenyl-modified bovine immunglobulin G (7 mol of DNP/mole of protein) had been polymerized into spherical particles. Antiserum directed to the dinitrophenyl group was added in strong dilution (10,000 - 500,000 times). On adding that antiserum to the particle suspension (5%, v/v) agglutination according to example 21 was obtained. This agglutination was inhibited when antiserum was present in the solution in amounts down to 2 ng/ml.

EXAMPLE 23

For the experiment of this example there were used micro particles consisting of polyacrylamide containing human serumalbumin corresponding to 15% of dry weight of the particles.

25 mg of particles were each suspended in a series of test tubes containing 1 ml of 0.005 M Na-phosphate buffer, 0.1 M NaCl pH 7.4, and salicyclic acid in a molar ratio between the salicyclic acid and the albumin varying from 0.1 to 2.0. After incubation for 10 minutes, the test tubes were centrifugated and the content of salicyclic acid in the supernatant was determined. A measure of the amount of salicyclic acid not bonded to the albumin in the particles for each added amount of salicyclic acid was obtained. The values were drawn in a so-called Scatchard-plot from whch a value for the association constant ($= 0.3 \times 10^5 M^{-1}$) of the salicyclic acid to the albumin could be read off.

EXAMPLE 24

The experiment of this example was carried out in a manner similar to example 23 except that warfarin was substituted for salicyclic acid. The association constant was $0.2 \times 10^6 M^{-1}$.

EXAMPLE 25

The experiment of this example was carried out in a manner similar to example 23 except that thyroxin was substituted for salicylic acid and globulin capable off binding tyroxin (TB G) obtained from human blood plasma was substituted for the human serum albumin.

What is claimed is:

1. A biologically active composition comprising microporous, spherical particles in gel form, said particles having a three-dimensional polymeric network, diameters less than 10 μm and an average diameter of from 0.5 to 4μm and a biologically active macromolecular substance immobilized within the meshes of said polymeric network but retainining its biological activity.

2. A biologically active composition according to claim 1 wherein the spherical particles consist of a copolymer of a low-molecular acrylic compound or of 1-vinyl-2-pyrrolidinone with a low-molecular divinyl compound.

3. A biologically active composition according to claim 2 wherein the spherical particles consist of a copolymer of an acrylamide of the formula

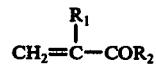

wherein R$_1$ is hydrogen or methyl and R$_2$ is OH or —NHR$_3$, wherein R$_3$ is hydrogen or a straight or branched alkyl group of 1-6 carbon atoms, which alkyl group is unsubstituted or substituted with a hydroxyl or an oxo group, with N,N'-methylene-bis-acrylamide.

4. A process for carrying out a bioassay for quantitatively determining a particular substance in a biological sample comprising adding to said sample a reagent comprising of a biologically active composition comprising
   a. microporous, spherical particles in gel form, said particles having a three-dimensional polymeric network, diameters less than 10 μm and an average diameter of from 0.5 to 4 μm and
   b. a biologically active macromolecular substance immobilized within the meshes of said polymeric network but retaining its biological activity, said biologically active macromolecular substance being specific to said particular substance.

5. Process according to claim 4 wherein the average particle diameter is 1 μm.

6. Process according to claim 4 wherein the biologically active macromolecular substance is labelled with an atom or group capable of emitting radiation or with an enzyme or a group producing a color.

7. A process for labelling a biological member selected from the group consisting of cells, cell fragments, viruses, tissue structures having specific receptors and substances having specific surface conformations comprising contacting said member with a reagent comprising a biologically active composition comprising a. microporous, spherical particles in gel form, said particles having three-dimensional polymeric network, diameters less than 10 μm and an average diameter of from 0.5 to 4 μm and b. a biologically active macromolecular substance immobilized within the meshes of said polymeric network but retainings its biological activity, said biologically active macromolecular substance being specific to said member and being labelled with a radioactive atom, an enzyme or fluorophore.

8. Process according to claim 7 wherein the average particle diameter is 1 μm.

9. A method of separating a biological member selected from the group consisting of cells, cell fragments, viruses, tissue structures having specific receptors and substances having specific surface conformtions from a biological sample containing said member comprising mixing said biological sample with a reagent comprising a biologically active composition comprising a. microporous, spherical particles in gel form, said particles having a three-dimensional polymeric network, diameters less than 10 μm and an average diameter of from 0.5 to 4 μm and b. a biologically active macromoleeular substance immobilized within the meshes of said polymeric network but retaining its biological activity, said biologically active macromolecular substance being specific to said member and separating the resulting conjugate of said member-said reagent by physical means.

10. Method according to claim 9, wherein the average particle diameter is 1 μm.

11. Method according to claim 9 wherein the biologically active macromolecular substance is labelled with an atom or group capable of emitting radiation or with an enzyme or a group producing a color.

* * * * *